United States Patent
Mezger et al.

[11] Patent Number: 5,997,827
[45] Date of Patent: Dec. 7, 1999

[54] APPARATUS FOR STERILIZING SURFACES WITH HYDROGEN PEROXIDE

[75] Inventors: Ulrich Mezger, Corseaux; Christian Schmied, Ursellen, both of Switzerland

[73] Assignee: Nestec, S.A., Vevey, Switzerland

[21] Appl. No.: 09/107,849

[22] Filed: Jun. 30, 1998

Related U.S. Application Data

[62] Division of application No. 08/700,659, Aug. 9, 1996.

[30]    Foreign Application Priority Data

Aug. 11, 1995  [EP]  European Pat. Off. .............. 95202189

[51] Int. Cl.$^6$ ....................................... A61L 2/00

[52] U.S. Cl. .............................. 422/292; 53/425; 53/431; 53/432; 261/142; 422/105; 422/110; 422/302; 422/306; 422/307

[58] Field of Search ..................................... 422/292, 110, 422/105, 302, 306, 307; 53/425, 431, 432; 261/142

[56]    References Cited

U.S. PATENT DOCUMENTS

| | | | |
|---|---|---|---|
| 3,583,635 | 6/1971 | Lemelson | 239/145 |
| 4,511,538 | 4/1985 | Buchner et al. | 422/303 |
| 4,683,701 | 8/1987 | Rangwala et al. | 53/167 |
| 4,742,667 | 5/1988 | Muller et al. | 53/167 |
| 4,743,407 | 5/1988 | Apel et al. | 261/99 |
| 4,863,688 | 9/1989 | Schmidt et al. | 422/28 |
| 5,038,742 | 8/1991 | Uddin | 123/549 |
| 5,178,841 | 1/1993 | Vokins et al. | 422/298 |
| 5,258,162 | 11/1993 | Andersson et al. | 422/28 |

FOREIGN PATENT DOCUMENTS 1582060 12/1980 United Kingdom .............. A61L 2/00

*Primary Examiner*—Krisanne Thornton
*Attorney, Agent, or Firm*—Vogt & O'Donnell, LLP

[57]    ABSTRACT

An apparatus for sterilizing surfaces has a tube and a plurality of nozzles wherein a mixture of hot air and vaporized hydrogen peroxide is fed from the tube, which is heated and which includes a porous section for feeding vaporized hydrogen peroxide into hot air fed through the tube to provide a mixture of hot air and vaporized hydrogen peroxide, the mixture being fed from the tube to surfaces to be sterilized by the nozzles.

11 Claims, 2 Drawing Sheets

APPARATUS FOR STERILIZING SURFACES WITH HYDROGEN PEROXIDE

CROSS REFERENCE TO RELATED APPLICATION

This application is a divisional application of application Ser. No. 08/700,659 which was filed Aug. 9, 1996.

BACKGROUND OF THE INVENTION

The present invention relates to sterilizing surfaces with hydrogen peroxide and particularly with a mixture of air and gaseous hydrogen peroxide and more particularly, to apparatus for effecting the same.

The sterilisation of packaging materials with gaseous hydrogen peroxide is well known in the art. The European Patent Application Publication No. 0 481 361 concerns an apparatus for sterilising containers which comprises a nozzle as the source of liquid hydrogen peroxide and heated air for vaporising said hydrogen peroxide. The drawback of this system is that the use of a nozzle for introducing the liquid hydrogen peroxide leads to e tendency for blocking said nozzle, and secondly, it is more difficult to enable uniform atomisation and a complete vaporisation when droplets have to be vaporised. Furthermore, specific vaporisation chambers often require a high vaporisation temperature and the decomposition rate of hydrogen peroxide can be relatively high. Finally, the apparatus of the above-mentioned patent application is complicated, which makes the maintenance and cleaning more difficult and expensive.

SUMMARY OF THE INVENTION

The aim of the present invention is to overcome the above-mentioned drawbacks and particularly to provide a process and also to provide an apparatus for carrying out the process wherein a complete vaporisation of the aqueous hydrogen peroxide, a constant concentration of hydrogen peroxide in the vapour-phase and a minimised decomposition of hydrogen peroxide can be guaranteed.

This invention provides a process for continuously sterilizing surfaces with a mixture of air and gaseous hydrogen peroxide wherein a stream of hot air is fed through a feeding tube to the surfaces to be sterilised, characterized in that, the hot air is mixed with completely vaporised hydrogen peroxide, wherein the vaporised hydrogen peroxide is diffused from a porous section of the feeding tube into the hot air stream to provide a hot air and vaporised hydrogen peroxide mixture to nozzles which feed the mixture to surfaces for sterilising the surfaces, said vaporized hydrogen peroxide being obtained by forming a thin film of liquid hydrogen peroxide in a porous tube section and by heating it, said porous tube section forming part of the hot air feeding tube and diffusing said vaporized hydrogen peroxide into the hot air stream.

The process according to the present invention takes advantage of the fact that heat and mass transfer during evaporation are considerably higher when a thin film of liquid is in contact with a hot surface, compared to the above-mentioned European '361 Application technology with evaporation of droplets in a hot air stream. Therefore, the formation of a well-spread thin film of liquid hydrogen peroxide is ensured by using a porous tube.

The invention further provides an apparatus for continuously sterilising containers in an aseptic filling line wherein the apparatus comprises a tube and a plurality of nozzles wherein a mixture of hot air and vaporised hydrogen peroxide is fed from the tube through nozzles to surfaces to be sterilised, wherein the tube includes a porous tube section for feeding, directly, the gaseous hydrogen peroxide into a stream of hot air, the tube being surrounded by a heating means.

DETAILED DESCRIPTION OF THE INVENTION

According to the present invention, "under surfaces" is to be understood as any type of enclosures, such as packagings made with any type of packaging material, such as glass, plastic, or metal.

The normal temperature of vaporisation of hydrogen peroxide in aqueous phase is about 107° C. with approximately 35% hydrogen peroxide in weight. The vaporisation of the hydrogen peroxide is performed at a temperature of from 110 to 130° C. of the heating equipment. The temperature must be high enough to guarantee the vaporisation of all the hydrogen peroxide, but not too high to avoid a decomposition of said $H_2O_2$. Typically, the temperature of heating equipment is around 120° C.

The process according to the invention is continuous and taking in account the new way of vaporisation, the consumption of hydrogen peroxide can be reduced. The concentration of hydrogen peroxide is from 5 to 20 mg/liter of air.

To prevent the gaseous hydrogen peroxide from condensing, the whole apparatus is kept at a temperature of the order of 120° C. The hot air stream is generated by means of a low pressure ventilator and a simple heat exchanger and can be easily monitored using a flow meter.

After the sterilisation step, according to the concentration of the hydrogen peroxide, condensation of said hydrogen peroxide can occur, and in this case, it is preferred to remove these residues and to have a drying air flow arriving on the sterilised surfaces at a temperature of the order of 120° C.

It is also preferable according to the invention to be sure that an efficient sterilisation effect can be guaranteed, and it is therefore preferable to have means for monitoring the temperature, the hot air flow rate and the hydrogen peroxide concentration of the gaseous mixture. The hot air flow rate depends on the diameter of the feeding tube and on the number of containers which has to be sterilised on the line. Normally, the air rate is from 20 to 50 l/min per container. Concerning the hydrogen peroxide concentration, it is measured on-line by means of a photometer or a system based on the thermal effect of a catalytic decomposition of hydrogen peroxide, wherein a small part of the stream of hydrogen peroxide is sucked through the measuring device (photometer or catalyst) using a small vacuum pump, which is explained in more detail hereunder.

As already said before, it is preferred that the hydrogen peroxide is totally vaporized at the moment of mixing with the hot air.

The porous tube is a sintered metal tube, for example made from stainless steel having pores of a diameter of 20 to 80 microns, preferably on the order of 40 microns. If the pore size is below 20 microns, large pumping pressures are required for the liquid hydrogen peroxide and the pores run the risk of becoming blocked. On the contrary, if the pore size is too great, this leads to the risk that not all the hydrogen peroxide is vaporised.

The thickness of the porous tube should be selected carefully for best results. In thin tubes, the contact period is not sufficient for allowing vaporisation and in tubes which are too thick, too great a decomposition of the hydrogen peroxide can occur. The best thickness is from 3 to 4 mm. Concerning the length, it must be sufficient to allow an adequate flow rate and evaporation of the hydrogen peroxide, leading to an efficient concentration in the stream of hot air, the optimal length being 15 to 30 cm.

The liquid hydrogen peroxide is in aqueous solution. The concentration is not critical, but is preferably between 5 and 45%, preferably about 35%. As already mentioned above, it is preferred to prevent any possibility of condensation, for example of steam coming from the water of the hydrogen peroxide, and the feeding tube is therefore steam heated at a temperature to about 120° C.

In the case of an apparatus which could be operated under ultrahygienic conditions, it would be also possible to reduce the hydrogen peroxide to as low as 0; the sterilization efficiency is reduced to vegetative germs only compared with a reduction of the thermophilic spores for hydrogen peroxide, and it necessitates a heating of the feeding tube as high as 170° C.

In the device according to the invention, the feeding of the gaseous hydrogen peroxide occurs through one feeding inlet or several, depending on the machine capacity. The diameter of the feeding tube of hot air is correspondingly increased.

To measure the hydrogen peroxide concentration, the apparatus comprises further a photometer or a system based on the catalytic decomposition of hydrogen peroxide.

Hydrogen peroxide shows a characteristic absorption peak at a wavelength of 200 nm. A standard photometer is combined with a vacuum pump, which guarantees a constant flow of the test gas through the measuring cell. To keep the test gas above the dew point, cylindrical and heated measuring cells are used.

The thermal effect of the catalytic decomposition of hydrogen peroxide can easily be measured by means of a small catalyst. A constant small part of the gas flows through a little catalyst that consists of a ceramic wafer material that is kept at a temperature of 120° C. Due to the exothermic decomposition of the gaseous hydrogen peroxide into oxygen and water, a significant temperature increase of the test gas can be measured between the inlet and the outlet of the catalyst. This temperature increase can be exactly correlated with the hydrogen peroxide concentration.

The apparatus according to the invention gives a tubular distribution system for the $H_2O_2$ vapour, without any valve, orifices or other components, built in. The correct gas distribution to the individual surfaces is assured by exchangeable nozzles, which can be calibrated at the corresponding outlets, to ensure amount of gas wanted at the specific place.

Both these control systems are appropriate for the continuous monitoring of the hydrogen peroxide vaporization quality and the sterilisation effect during production.

An embodiment of the invention is described with reference to the accompanying drawings.

BRIEF DESCRIPTION OF THE DRAWING FIGURES

DETAILED DESCRIPTION OF THE DRAWING FIGURES

Figure 1:
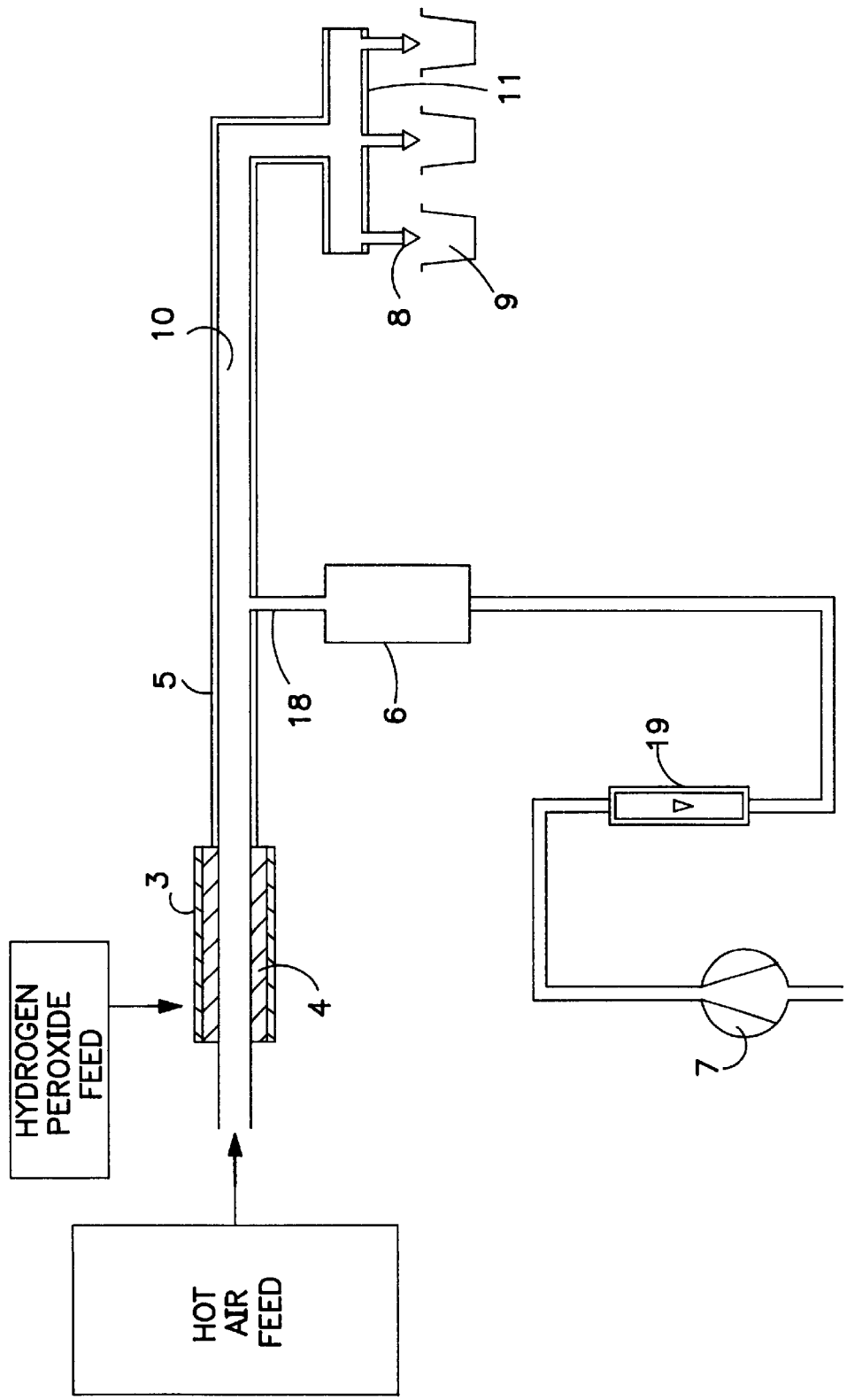
FIG. 1 shows a schematic view of the apparatus according to the invention.

FIG. 1 demonstrates the principle of a package sterilization by means of the hydrogen peroxide vaporiser which, as illustrated, includes an elongated outer surface opposed by an elongated inner surface about a tube hollow which defines and thereby contains one elongated tube passage. The liquid hydrogen peroxide, represented in FIG. 1 by a labelled box and arrow, is fed directly onto the porous tube section (4) by means of a positive pump (not shown), said peroxide being vaporised by means of the steam jacket (3) heating the porous tube. The hot air stream, represented in FIG. 1 by a labelled box and arrow, is generated by means of a conventional low pressure system (not shown). To prevent the gaseous hydrogen peroxide and the steam from condensation, the feeding tube (10) is heated with a steam jacket (5). The packages (9) to be sterilized are disposed directly under the corresponding nozzles (8) diffusing the mixture of hot air and gaseous hydrogen peroxide. A measuring device (6), such as a photometer, is disposed on-line via piping (18), as illustrated, to control the concentration of the hydrogen peroxide in the line, a measured part controlled by a flow meter (19) of the main stream being sucked through said measuring device with the help of a small vacuum pump (7). The nozzles (8) are also equipped with a steam jacket (11), avoiding therefore any risk of condensation in the whole sterilising apparatus.

Figure 2:
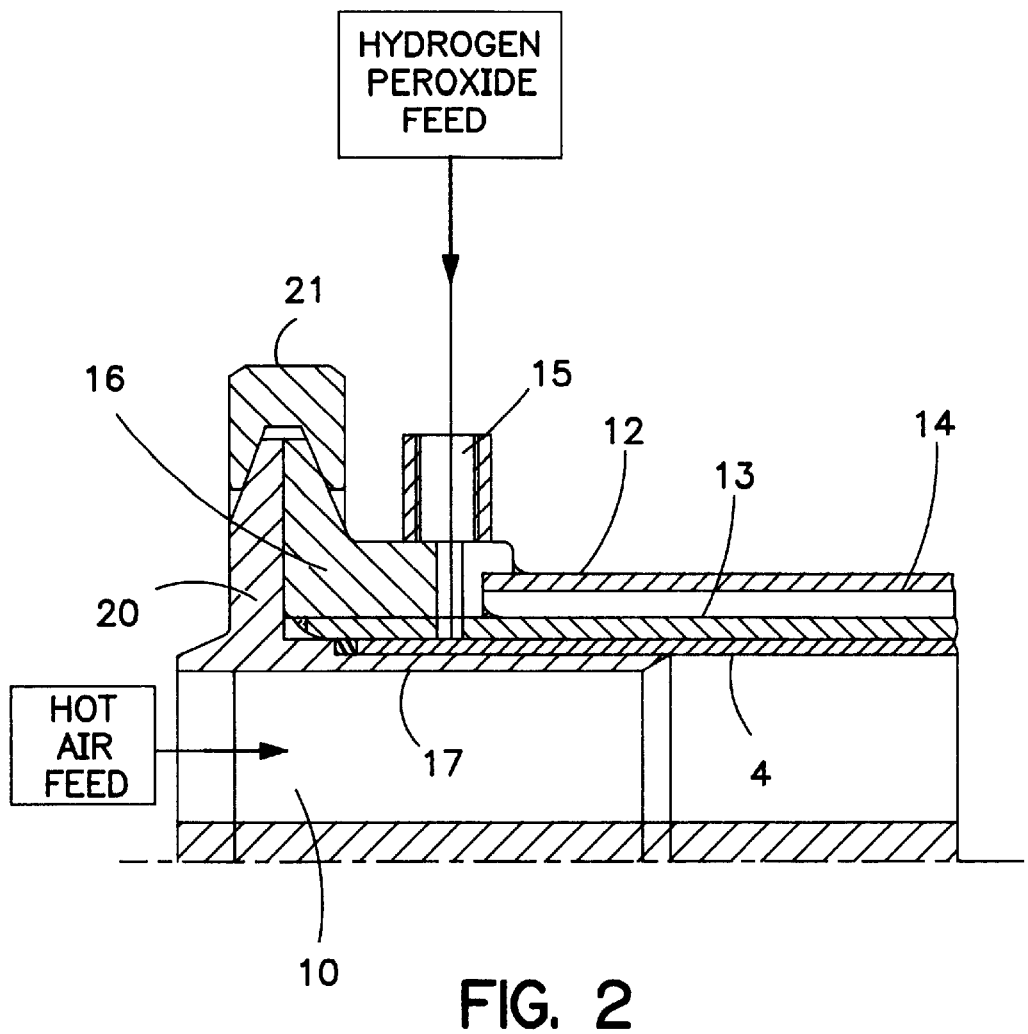
FIG. 2 shows a cross section of a portion of the apparatus of FIG. 1.

In operation and with reference to FIG. 2, the steam jacket of the vaporizer comprises two concentric tubes (12,13), which are heated by steam, at a temperature of 120° C., flowing through the channel (14). The liquid hydrogen peroxide, represented in FIG. 2 by a labelled box and arrow, arriving through inlet (15) diffuses through the porous tube (4), where it is totally vaporized by the heating of tube (13), and enters the feeding tube (10) and mixes with the arriving hot air stream, represented in FIG. 2 by a labeled box and arrow, fed to and within and longitudinally through tube (10). The vaporizer comprises further a connecting part (16), which is necessary for allowing said vaporizer to be disposed in the feeding tube (10). A second part (20) comprises an extension (17) for preventing the liquid hydrogen peroxide from directly dripping into the air stream. A connecting ring (21)joins the connecting part (16) with the part (20). Taking in account the presence of the steam jackets (5,11), no condensation occurs, and also with reference to FIG. 1, the mixture of air and hydrogen peroxide flows through the feeding tube (10) at the nozzles (8) to sterilise the containers (9), which are then ready to go to the drying stage (not shown) and finally, under the aseptic filling nozzle. Three seconds are normally necessary for the sterilization of each container.

In the case of an apparatus operating with several inlets (15), the presence of the extension (17) is no more useful.

EXAMPLE

The apparatus of FIGS. 1–2 is used with hydrogen peroxide at a concentration of 35% and operating with a steam jacket at 120° C. for the sterilization of containers (volume of 200 ml) for aseptic applications. A concentration of the hydrogen peroxide in the gaseous mixture of 10 mg/liter of air is used.

The nozzle (8) operates at 30 l/min. to reach a decimal reduction of 5 D with Bac. subtilis, var. globigii and exposure time of 3 sec.

We claim:

1. An apparatus for sterilizing a surface wherein the apparatus comprises:

a tube structure which comprises an elongated outer surface opposed by an elongated inner surface about a tube hollow to define one hollow elongated tube passage for passage of hot air and which comprises, for a portion of its length, a tube section which is porous for diffusing hydrogen peroxide fed to the outer surface and into the passage via the inner surface for feeding vaporized hydrogen peroxide into the passage for mixture with hot air passed in the passage past the porous section;

means for heating the tube structure to a temperature for vaporizing liquid hydrogen peroxide;

a plurality of nozzles connected with the tube structure at a position for receiving, from the passage, a mixture of hot air and vaporized hydrogen peroxide passed in the passage past the porous section for feeding the mixture from the tube structure to surfaces for sterilizing the surfaces; and wherein the elongated passage is the only elongated passage contained within the tube structure.

2. An apparatus according to claim 1 wherein the means for heating the tube structure comprises a jacket which surrounds the porous tube section for supplying heat to the porous tube section.

3. An apparatus according to claim 1 wherein the tube structure comprises a further section which extends from the porous tube section and wherein the nozzles are connected to the further section and wherein the means for heating the tube structure comprise a jacket which surrounds the porous tube section and a jacket which surrounds the further section for supplying heat to the porous tube section and the further tube section.

4. An apparatus according to claim 1 or 2 or 3 further comprising a jacket positioned for supplying heat to each nozzle.

5. An apparatus according to claim 1 or 2 or 3 further comprising means for generating hot air and for feeding the hot air generated to the tube structure for passing the hot air in the passage past the porous tube section to obtain the mixture of the hot air and vaporized hydrogen peroxide.

6. An apparatus according to claim 4 further comprising means for generating hot air and for feeding the hot air generated to the tube structure for passing the hot air in the passage past the porous tube section to obtain the mixture of the hot air and vaporized hydrogen peroxide.

7. An apparatus according to claim 1 wherein the porous tube section is comprised of sintered metal.

8. An apparatus according to claim 1 wherein the porous tube section has pores having a diameter of from 20 microns to 80 microns.

9. An apparatus according to claim 7 or 8 wherein the porous section has an outer surface to inner surface thickness of from 3 mm to 4 mm.

10. An apparatus according to claim 1 further comprising a photometer connected with the tube at a position for measuring hydrogen peroxide concentration in the hot air and vaporized hydrogen peroxide mixture in the tube.

11. An apparatus according to claim 1 wherein the means comprising a thermal catalytic decomposition catalyst connected with the tube at a position for measuring hydrogen peroxide concentration in the hot air and vaporized hydrogen peroxide mixture in the tube.

* * * * *

UNITED STATES PATENT AND TRADEMARK OFFICE
CERTIFICATE OF CORRECTION

PATENT NO. : 5, 997, 827
DATED : December 7, 1999
INVENTOR(S) : Urlich MEZGER, *et al.*

It is certified that error appears in the above-identified patent and that said Letters Patent is hereby corrected as shown below:

Column 4, line 21, insert a comma after "(8)" and then insert -- connected with a tube section at a position displaced a distance from the porous tube section and also from the piping (18) --.

Signed and Sealed this

Twenty-sixth Day of September, 2000

*Attest:*

Q. TODD DICKINSON

*Attesting Officer*         *Director of Patents and Trademarks*